(12) United States Patent
Delaney

(10) Patent No.: US 8,097,002 B2
(45) Date of Patent: Jan. 17, 2012

(54) ANOSCOPE FOR INSPECTION AND/OR SURGERY

(76) Inventor: Conor P. Delaney, Shaker Heights, OH (US)

(*) Notice: Subject to any disclaimer, the term of this patent is extended or adjusted under 35 U.S.C. 154(b) by 470 days.

(21) Appl. No.: 12/105,699

(22) Filed: Apr. 18, 2008

(65) Prior Publication Data

US 2008/0262511 A1 Oct. 23, 2008

Related U.S. Application Data

(60) Provisional application No. 60/912,502, filed on Apr. 18, 2007.

(51) Int. Cl.
*A61B 1/00* (2006.01)
(52) U.S. Cl. .......... 606/115; 600/105; 600/114
(58) Field of Classification Search .......... 600/101, 600/104–106, 109, 114, 127, 160, 175, 178–179, 600/184, 199; 606/39–40, 45–46, 140, 163
See application file for complete search history.

(56) References Cited

U.S. PATENT DOCUMENTS

| | | | | |
|---|---|---|---|---|
| 2,482,971 A * | 9/1949 | Golson | .......... | 600/184 |
| 4,690,132 A | 9/1987 | Bayer et al. | | |
| 6,015,937 A | 1/2000 | Branemark | | |
| 6,616,603 B1 * | 9/2003 | Fontana | .......... | 600/199 |
| 6,974,466 B2 * | 12/2005 | Ahmed et al. | .......... | 606/140 |
| 7,029,438 B2 | 4/2006 | Morin et al. | | |
| 2006/0009797 A1 | 1/2006 | Armstrong | | |
| 2006/0264706 A1 * | 11/2006 | Piskun | .......... | 600/105 |

FOREIGN PATENT DOCUMENTS

WO 2006033122 3/2006
WO 2007019321 2/2007

OTHER PUBLICATIONS

International Search Report in International Application No. PCT/US2008/005094; Feb. 9, 2008 (Day/Month/Year).
Supplementary European Search Report regarding EP 08 74 3119, dated Jun. 8, 2011.

* cited by examiner

*Primary Examiner* — Ryan Severson
*Assistant Examiner* — Ashley Cronin
(74) *Attorney, Agent, or Firm* — Benesch, Friedlander, Coplan & Aronoff LLP

(57) ABSTRACT

An anoscope for inspection and/or surgery is provided. The anoscope includes a tubular body having a distal end, a proximal end, and a longitudinal axis defined therebetween, where the tubular body includes at least one elongated slot. The anoscope also includes an insert removably attached to the at least one elongated slot in the tubular body. The insert including an elongated slot having a smaller width than the at least one elongated slot in the tubular body.

20 Claims, 5 Drawing Sheets

ND/OR SURGERY

CROSS-REFERENCE TO RELATED APPLICATION

This application claims priority to U.S. Provisional Application No. 60/912,502 filed on Apr. 18, 2007, the disclosure of which is hereby incorporated by reference in its entirety herein.

BACKGROUND

Hemorrhoid disease is an extremely common condition that causes persistent and severe symptoms, such as prolapse, bleeding, and discomfort. More rarely, hemorrhoids can become thrombosed, or ischemic and gangrenous, requiring emergency therapy. An estimated 4 million people per year have symptoms relating to hemorrhoids, while approximately one million seek treatment.

Traditional hemorrhoid management includes conservative therapies for minimally troubling hemorrhoid disease, with step-wise progression of invasive therapies for more symptomatic (usually larger) hemorrhoids. The next level of hemorrhoid therapy often utilizes rubber band ligation (generally, an office-based procedure), infra-red coagulation (not really proven or widely accepted), or sclerotherapy. Patients with persistent symptoms who fail these treatments require progression to operative surgery.

Operative hemorrhoid surgery is usually performed under general anesthesia as a day-case procedure. The traditional hemorrhoid surgery has been an excisional hemorrhoidectomy, most commonly a Ferguson or Milligan-Morgan procedure. These procedures are typically uncomfortable and usually require a procedure in the operating room.

More recently, the Procedure for Prolapsing Hemorrhoids (PPH) has been used to treat hemorrhoid disease. This procedure uses a circular stapler to excise a circular ring of tissue several centimeters inside the anal canal to retract the anoderm and reduce the hemorrhoids. In several studies, PPH has been shown to provide an equivalent outcome to excisional surgery, with pain scores that are significantly improved in the post-operative period (generally about 3-4 points lower than excisional hemorrhoidectomy on a 10 point VAS score). The disadvantages of PPH, however, are that i) the results are essentially no better than traditional hemorrhoidectomy (except for pain scores); ii) general anesthesia is required; iii) day-case hospital admission is required; iv) the circular stapler is a relatively expensive device (compared to cautery and absorbable suture for excisional hemorrhoidectomy); and v) PPH is a relatively new procedure that requires a new CPT code and requires surgeons to be specifically trained for this procedure. Furthermore, several serious complications of the PPH procedure have been described.

SUMMARY

An anoscope for inspection and/or surgery is provided. The anoscope includes a tubular body having a distal end, a proximal end, and a longitudinal axis defined therebetween, where the tubular body includes at least one elongated slot. The anoscope also includes an insert removably attached to the at least one elongated slot in the tubular body. The insert including an elongated slot having a smaller width than the at least one elongated slot in the tubular body.

A method of performing an excisional hemerrhoidectomy on a patient is also provided. The method includes the steps of: a) providing an anoscope that includes a tubular body having an elongated slot and an insert removably attached to the slot in the tubular body, the insert including an elongated slot having a smaller width than the elongated slot in the tubular body; b) inserting the anoscope into the anal canal of the patient; c) rotating the anoscope to align the elongated slot in the insert with a hemorrhoid in the anal canal of the patient; d) drawing the hemorrhoid through the elongated slot in the insert; e) excising the hemorrhoid; f) removing the insert from the tubular body to expose the elongated slot in the tubular body; and g) suturing the excision wound. Steps c-g can be repeated to excise additional hemorrhoids in the anal cavity of the patient.

A kit for performing an excisional hemerrhoidectomy on a patient is also provided. The kit includes an anoscope that includes a tubular body having an elongated slot and an insert removably attached to the slot in the tubular body, where the insert including an elongated slot having a smaller width than the elongated slot in the tubular body; a grasping instrument; and an excising device.

BRIEF DESCRIPTION OF THE DRAWINGS

It will be appreciated that the illustrated boundaries of components in the figures represent one example of the boundaries. One of ordinary skill in the art will appreciate that one component may be designed as multiple components or that multiple components may be designed as one component. Additionally, an internal component may be implemented as an external component and vice versa.

Further, in the accompanying drawings and description that follow, like parts are indicated throughout the drawings and description with the same reference numerals, respectively. The figures may not be drawn to scale and the proportions of certain parts have been exaggerated for convenience of illustration.

DETAILED DESCRIPTION

Figure 1A:
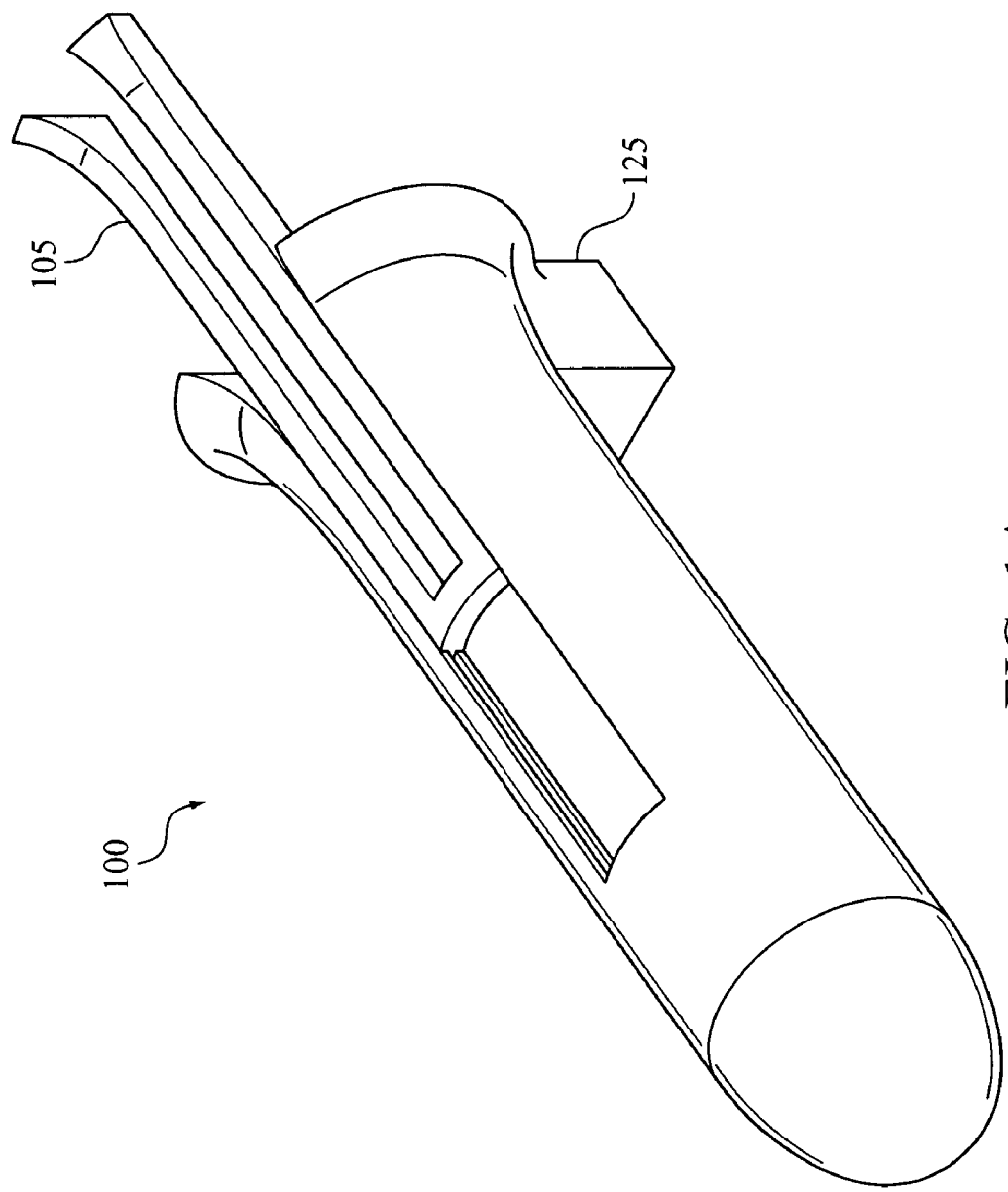
FIG. 1A illustrates a perspective view of one embodiment of an anoscope 100 including a removable insert 105.

Certain terminology will be used in the following description for convenience in reference only and will not be limiting. The terms "rightward" and "leftward" will refer to directions in the drawings in connection with which the terminology is used. The terms "upward" and "downward" will refer to directions as taken in the drawings in connection with which the terminology is used. The terms "inwardly" and "outwardly" will refer to directions toward and away from, respectively, the geometric centerline of the device. All foregoing terms mentioned above include the normal derivative and equivalents thereof.

The present application is directed to an anoscope for anal inspection and/or surgery. The anoscope can be used to facilitate an excisional hemorrhoidectomy, to facilitate the excision of lesions on hemorrhoids, or to facilitate any other anal or rectal surgery. In one embodiment, the anoscope has a first elongated slot that is configured to receive a removable insert having a second elongated slot, which has a smaller width than the first elongated slot. The second elongated slot (i.e., the narrower slot) is sized to permit a surgeon to safely and rapidly isolate a certain portion of the hemorrhoid or the entire hemorrhoid that the surgeon desires to excise. Upon removal of the insert, the first elongated slot (i.e., the wider slot) is sized to permit the surgeon to suture the excision wound. Thus, the narrower slot permits the hemorrhoid to be extruded into the anoscope and safely excised, without excision of an inappropriate amount of tissue and without excision of anal sphincter muscle. The wider slot then permits direct visualization of the wound for suturing thereof.

Illustrated in FIG. 1A is a perspective view of one embodiment of an anoscope 100 for anal inspection and/or surgery. The anoscope 100 includes a removable insert 105, which will be described in further detail below.

Figure 1B:
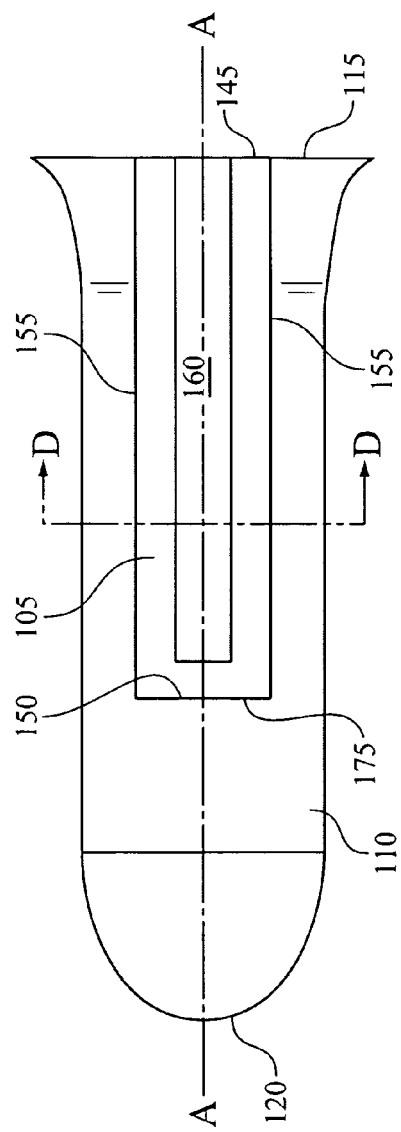
FIG. 1B illustrates a top plan view of the anoscope 100 with the insert 105 in an attached position.
Figure 1C:
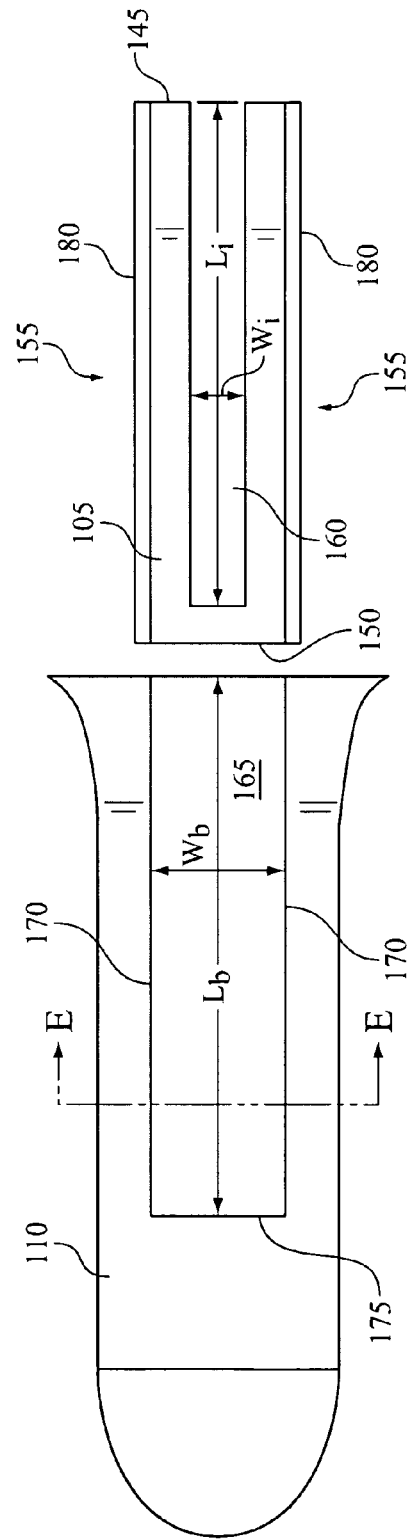
FIG. 1C illustrates a top plan view of the anoscope 100 with the insert 105 in a detached position.

Illustrated in FIGS. 1B and 1C are top plan views of the anoscope 100 with the insert 105 in attached and detached positions, respectively. The anoscope 100 includes a tubular body 110 having a proximal end 115, a distal end 120, and a central longitudinal axis A that extends therebetween. In the illustrated embodiment, the distal end 120 is closed and anatomically contoured to facilitate insertion of the anoscope 100 into the anal canal of a patient, while the proximal end 115 is open and flared to limit insertion of the anoscope 100 into the anal canal and so that internal and external components of the hemorrhoid can protrude into the anoscope 100 equally. In an alternative embodiment (not shown), the distal end 120 can be open to accommodate a removable obturator that is used to introduce the anoscope into the anal canal. Moreover, in alternative embodiment (not shown), the anoscope 100 can include two or more removable inserts each having an elongated slot.

With reference to FIG. 1A, the anoscope 100 includes a handle 125 (not shown in its entirety) extending radially outward from the tubular body 110 adjacent the proximal end 115 of the tubular body 110. The handle 125 is sized to be grasped by a surgeon's hand and configured to permit the surgeon to insert, withdraw, and/or rotate the anoscope 100.

Figure 1E:
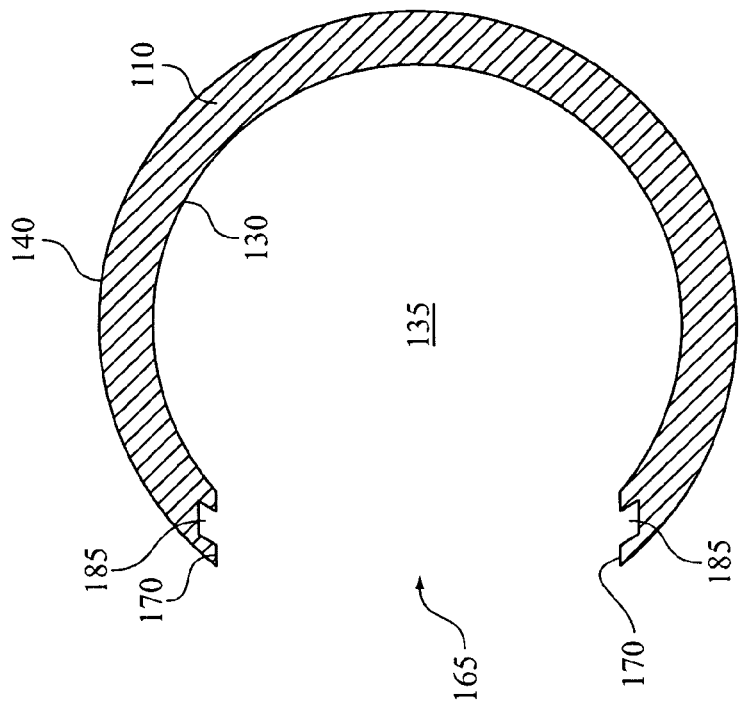
FIG. 1E illustrates an enlarged cross-sectional view of the anoscope 100 taken across line E-E.
Figure 1D:
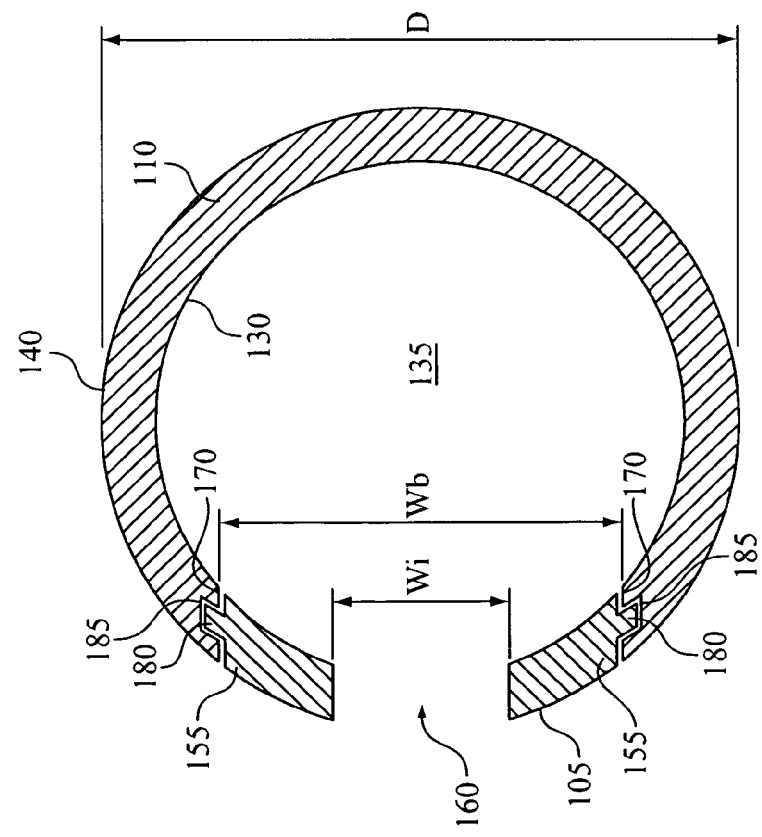
FIG. 1D illustrates an enlarged cross-sectional view of the anoscope 100 taken across line D-D.

Illustrated in FIG. 1D is an enlarged cross-sectional view of the anoscope 100 taken along line D-D. As shown in FIG. 1D, the tubular body 110 has an inner surface 130, which defines a cylindrically-shaped cavity 135, and an outer surface 140, which has an outer diameter D that is sized for an average anal canal. In one embodiment, the outer diameter D of the outer surface 140 of the tubular body 110 is between about 30 mm and about 35 mm. In other embodiments, the outer diameter D of the outer surface 140 of the tubular body 110 can be between about 25 mm and about 40 mm.

With reference back to FIGS. 1B and 1C, the anoscope 100 includes an insert 105 that is removably attached to the tubular body 105 as discussed above. The insert 105 is axially movable between an attached position (FIG. 1B) and a detached position (FIG. 1C), where the insert 105 is completely removed from the tubular body 110 of the anoscope 100. In the illustrated embodiment, the insert 105 is generally rectangular shaped when viewed from the top and includes a proximal end 145 that is coincident with the proximal end 115 of the tubular body 110, a distal edge 150, and a pair of side edges 155 extending therebetween. In alternative embodiments (not shown), the insert 105 can take the form of a variety of shapes when viewed from the top.

It will be appreciated that, since the proximal end 145 of the insert 105 in the illustrated embodiment is coincident with the proximal end 115 of the tubular body 110, the proximal end 145 of the insert 105 includes a flared portion that can serve as a grasping feature to assist the surgeon in removing the insert 105 from the tubular body 110. Optionally, the insert 105 can include a tab (not shown) or another grasping feature (not shown) extending from the insert 105 to facilitate easy removal of the insert 105 from the tubular body 110.

As shown in FIG. 1C, the insert 105 further includes an elongated slot 160 that extends from the proximal end 145 towards the distal end 150 of the insert 105, such that the insert has a U-shape when viewed from the top, and is in communication with the cavity 135 when the insert 105 is attached to the tubular body 110. The slot 160 is sized to permit the surgeon to introduce a hemorrhoid through the slot 160 and into the cavity 135 in order to isolate and subsequently excise the hemorrhoid, which will be described in further detail below. Because of this, the slot 160 may hereinafter be referred to as the "excision slot 160". In the illustrated embodiment, the excision slot 160 is rectangular-shaped having a width $W_i$ and a length $L_i$. In one embodiment, the excision slot 160 can have a width $W_i$ between about 6 mm and about 8 mm and a length $L_i$ between about 5 mm and about 13 mm. In alternative embodiments, the excision slot 160 can have a width $W_i$ between about 50 mm and about 80 mm and a length $L_i$ between about 40 mm and about 120 mm.

In alternative embodiments (not shown), the excision slot 160 can take the form of other shapes when viewed from the top (e.g., the distal end of the excision slot 160 can be rounded). Additionally, in another embodiment (not shown), the excision slot 160 can stop short of the proximal end 145 of the insert 105. In other words, the proximal end of the excision slot 160 can be spaced inward from the proximal end 145 of the insert 105.

Illustrated in FIG. 1E is an enlarged cross-sectional view of the anoscope 100 taken along line E-E. When the insert 105 is removed from the tubular body 110 (i.e., the insert 105 is detached), an elongated slot 165 corresponding to the size and shape of the insert 105 is present in the tubular body 110 as shown in FIG. 1E (and FIG. 1C). The elongated slot 165 extends from the proximal end 115 toward the distal end 120 of the tubular body 110 and is in communication with the cavity 135 when the insert 105 is detached from the tubular body 110. The slot 165 is defined in the tubular body 110 by a pair of side walls 170 and an end wall 175, and is sized to permit the surgeon to suture the wound after a hemorrhoid has been excised, which will be described in further detail below. Because of this, the slot 165 may hereinafter be referred to as the "suture slot 165".

In the illustrated embodiment, the suture slot 165 is rectangular-shaped when viewed from the top and has a width $W_b$ and a length $L_b$. In one embodiment, the suture slot 165 can have a width $W_b$ between about 12 mm and about 20 mm and a length $L_b$ between about 50 mm and about 80 mm. In alternative embodiments, the suture slot 165 can have a width $W_b$ between about 10 mm and about 22 mm and a length $L_b$ between about 40 mm and about 120 mm. In all cases, the width $W_i$ of the excision slot 165 in the insert 105 is less than the width of the width $W_b$ of the suture slot 165 in the tubular body 110 to limit the amount of tissue that will be excised during a hemorrhoidectomy. In alternative embodiments (not shown), the suture slot 165 can take the form of other shapes when viewed from the top (e.g., the distal end of the suture slot 165 can be rounded).

As discussed above, the insert 105 is removably attached to the tubular body 110. In the illustrated embodiment, the insert 105 is slidably attached to the tubular body 110 via a tongue and groove arrangement. Specifically, the side edges 155 of the insert 105 each include a tongue 180 configured for receipt by a corresponding groove 185 in the side edges 170 of the tubular body 105 as shown in FIGS. 1D and 1E. Optionally, the distal edge 150 of the insert 105 includes a tongue (not shown) configured for receipt by a corresponding groove in the end wall 175 of the tubular body 110. In this arrangement, the insert 105 can slide in an axial direction relative to the tubular body 110. It will be appreciated that the tongue and groove arrangement can be reversed, such that the grooves can be provided in the side and/or distal edges of the insert 105 and the tongues can be provided on the side and/or end walls of the tubular body 110. Moreover, it will be appreciated that any male/female structure or any other known removable attachment means can be used to permit the insert 155 to be removably attached to the tubular body 110.

The anoscope 100 can be constructed from a variety of materials. In one embodiment, the anoscope 100 can be constructed from a polymeric material, which is inert and biologically safe, so that it can be disposable. In other embodiments, the anoscope can be constructed from a metal material, such as stainless steel, so that it can be reusable.

Optionally, the anoscope 100 may include a light source (not shown), such as a fiber optic light pipe or directional light source, positioned within the cavity 135 to illuminate the tissue adjacent to the excision slot 160 in the insert 105 when the insert 105 is attached to the tubular body 110 and to illuminate the tissue adjacent to the suture slot 165 in the tubular body 110 when the insert 105 is detached from the tubular body 110. The light source may be mounted to the inner surface 130 of the tubular body 110 or may be introduced into the cavity 135 from an external source.

Optionally, the anoscope 100 may include a suction device (not shown) positioned within the cavity 135 to prevent impairment of the surgeon's view by smoke if using cautery. The suction device may be mounted to the inner surface 130 of the tubular body 110 or may be introduced into the cavity 135 from an external source.

An exemplary method of using the anoscope described above to perform an excisional hemorrhoidectomy is discussed below.

Initially, the patient is anesthetized with local anesthesia, sedation, or general anesthesia as per the surgeon's and patient's preference. The anus and perianal skin are then prepped and draped routinely with antiseptic agents and drapes. Using lubricant, the surgeon inserts the anoscope 100, with the insert 105 attached, into the anal canal of the patient and rotates it until the first hemorrhoid H that is being excised is aligned with the excision slot 160 in the insert 105.

Figure 2C:
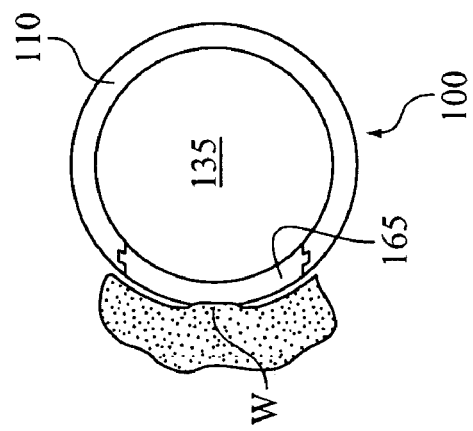
FIGS. 2A-2C illustrate end views looking into the open proximal end 115 of the anoscope 100 at various stages during an exemplary excisional hemerrhoidectomy.
Figure 2B:
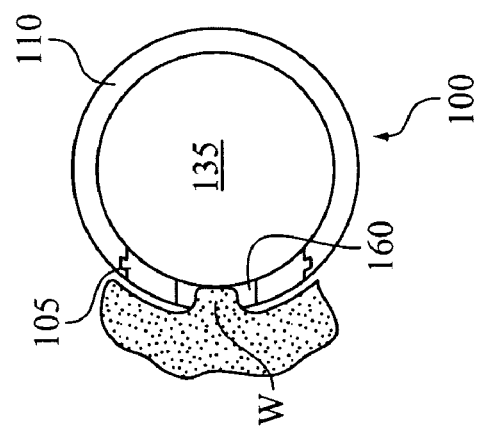
Figure 2A:
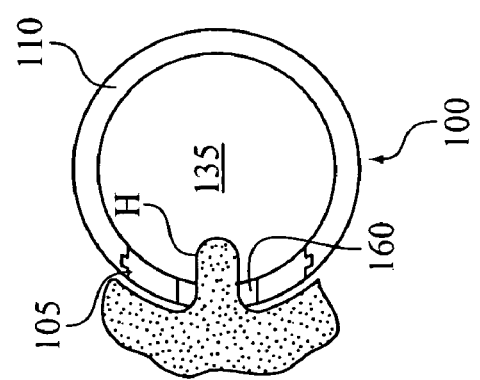

Once the excision slot 160 in the insert 105 is aligned with the hemorrhoid to be excised, the surgeon grasps the hemorrhoid H using a grasping instrument (e.g., an instrument similar to an angled bowel clamp) and draws it through the excision slot 160 in the insert 105 and into the cavity 135 of the anoscope 100, thereby isolating the internal and external hemorrhoid H into the cavity 135 of the anoscope 100 (FIG. 2A). It is noted that the hemorrhoid H should be drawn into the cavity 135 of the anoscope 100 under appropriate tension to determine how much of the hemorrhoid H needs to be excised. Then, the surgeon holds the hemorrhoid H in place with a holding instrument (such as a Kelly clamp or even a specifically designed clamp).

Next, the surgeon excises the hemorrhoid H using an excising device (FIG. 2B). It should be noted that several passes may be necessary to excise the hemorrhoid, starting distally at the external component, if present, and working proximally to the apex of the internal component. The excising device may be mechanical (e.g., a blade) or energy source-based (e.g., an ultrasonic ablation device such as the harmonic scalpel or Ligasure, a radiofrequency ablation device, or an electric current cautery device). Preferably, the excising device provides hemostasis after the excision of the hemorrhoid. Alternatively, a stapler may be used, but would likely require absorbable staples. Due to the fact that the excision slot 160 in the insert 105 has a smaller width than the suture slot 165 in the tubular body 110, the anoscope 100 limits the amount of tissue that can be drawn in and subsequently excised, thereby preventing, or at least minimizing, risk to the anal sphincter and risk of anal stenosis.

After the hemorrhoid has been excised, the insert 105 is removed from the anoscope 100 while the anoscope 100 is still present in the anal canal of the patient, thereby exposing the wider suture slot 165 in the tubular body 110 to the resultant excisional wound W (FIG. 2C). The suture slot 165 provides easier access to the excision wound W, with a margin of, for example, several millimeters on each side of the wound W. The wound W may then be sutured, generally using an absorbable suture (e.g., a 2/0 polyglycolic acid suture), to support the wound W from early breakdown or dehiscence, and possibly accelerates healing and reduces risk of bleeding.

After the wound W has been sutured, the insert 105 is then replaced on the anoscope 100 and the above procedure can be repeated for additional hemorrhoids, if any. Once all of the hemorrhoids have been excised, hemostasis is confirmed at all sites and the patient can be discharged with standard post-operative instructions.

There are several potential advantages to the anoscope 100 described above and illustrated in the figures. First, by enabling the anoscope to be present within the anal canal at all times, the possibility of anal stenosis from excision of too much hemorrhoid and sphincter injury from damage to the sphincter by surgeons taking too much tissue during hemorrhoid excision is minimized. Second, the anoscope is designed to be able to facilitate high volume hemorrhoidectomy procedures in the out-patient setting, dealing with everything from minor grade one hemorrhoids to large grade 3 hemorrhoidal disease and coping with internal and external components. Third, since the exemplary procedure described above is similar to a traditional hemorrhoidectomy, the transfer of skills for surgeons who are in practice and who have undergone general surgical training is made easier. This essentially makes excisional hemorrhoidectomy easier and safer than the current procedure, using the same excisional hemorrhoidectomy code.

Figure 3A:
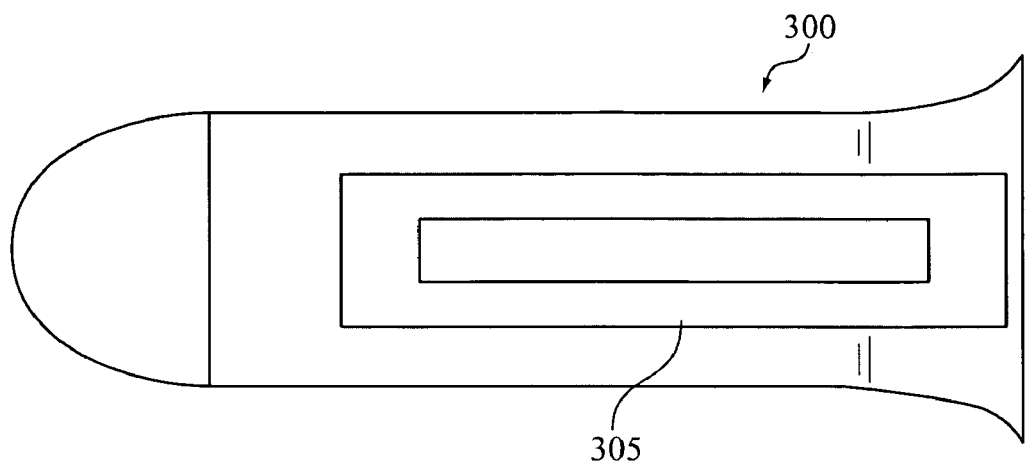
FIG. 3A illustrates a top plan view of another embodiment of an anoscope 300 including a removable insert 105 with the insert 305 in an attached position.
Figure 3B:
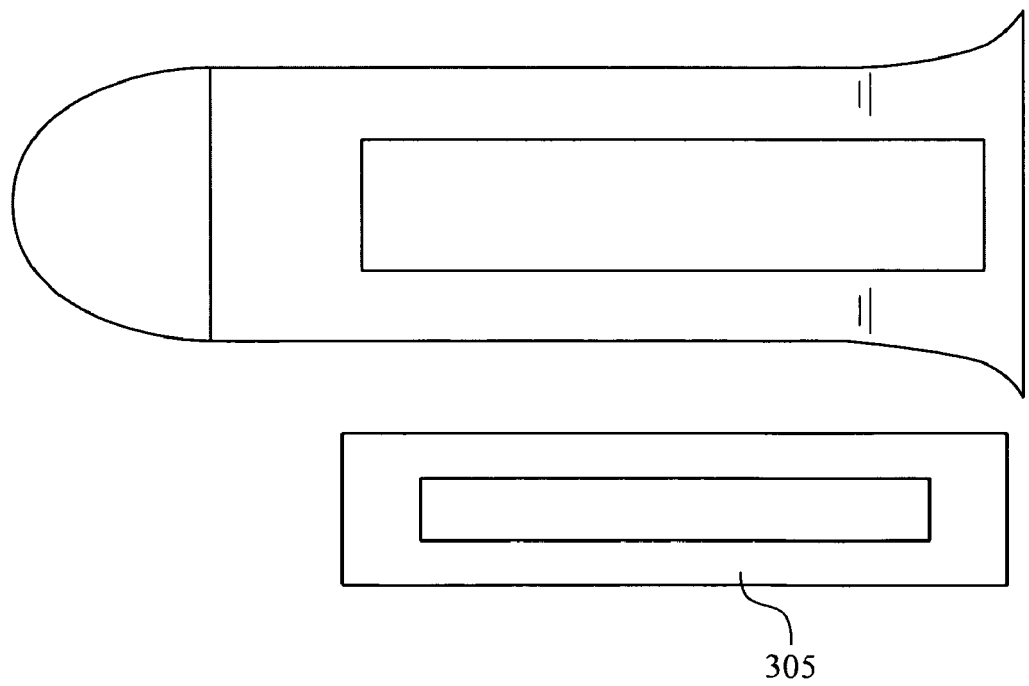
FIG. 3B illustrates a top plan view of the anoscope 300 with the insert 305 in a detached position.

Illustrated in FIGS. 3A and 3B are top plan views of another embodiment of an anoscope 300 having a removable insert 305 in attached and detached positions, respectively. The anoscope 300 is similar in structure to the anoscope 100 described above and illustrated in FIGS. 1A-1E, with the exception that the removable insert 305 is removably attached to the anoscope 300 via a snap-fit or other similar connection means. The anoscope 300 functions in the same manner as the anoscope 100 described above and illustrated in FIGS. 1A-1E, except that the anoscope would need to removed from the patient's anal canal in order to remove the insert 305 from the anoscope 300.

It is also contemplated that the anoscope can be packaged as part of a disposable kit to enable a surgeon to perform an excisional hemorrhoidectomy. The kit could include either of the anoscopes shown and described above, a grasping instrument for grasping the hemorrhoid such as the one discussed above, and an excising device such as the ones described above.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or multiple components.

While the present application illustrates various embodiments, and while these embodiments have been described in some detail, it is not the intention of the applicant to restrict or in any way limit the scope of the claimed invention to such detail. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's claimed invention. Moreover, the foregoing embodiments are illustrative, and no single feature or element is essential to all possible combinations that may be claimed in this or a later application.

What is claimed is:

1. An anoscope for inspection and/or surgery, the anoscope comprising:
    a tubular body having a distal end, a proximal end, a longitudinal axis defined therebetween, an outer surface, and an inner surface defining a cavity, the tubular body having at least one elongated opening from the outer surface to the cavity, beginning at the proximal end of the tubular body and extending towards and terminating before the distal end of the tubular body;
    an insert removably attached to the at least one elongated opening in the tubular body via a tongue and groove arrangement, the insert having an outer surface and an inner surface and including an elongated opening from the outer surface through the inner surface, the elongated opening of the insert beginning at a proximal end of the insert and extending towards and terminating before a distal end of the insert, such that the insert has a U-shape when viewed from the top, the elongated opening of the insert having a smaller width than the at least one elongated opening in the tubular body.

2. The anoscope of claim 1, wherein the proximal end of the tubular body is generally open and the distal end of the tubular body is generally closed.

3. The anoscope of claim 1, wherein the proximal end of the tubular body includes a flared portion.

4. The anoscope of claim 1, wherein the at least one elongated opening in the tubular body is generally rectangular when viewed from the top.

5. The anoscope of claim 1, wherein the elongated opening in the insert is generally rectangular when viewed from the top.

6. The anoscope of claim 1, further comprising a handle extending from the proximal end of the tubular body.

7. The anoscope of claim 1, wherein the insert includes a pair of side edges, each of which has a tongue for receipt within a respective groove in the at least one elongated opening of the tubular body, to permit axial movement of the insert relative to the tubular body.

8. The anoscope of claim 1, further comprising a light source positioned within the tubular body.

9. The anoscope of claim 1, further comprising a suction device positioned within the tubular body.

10. The anoscope of claim 1, wherein the at least one elongated opening in the tubular body includes a pair of side edges, each of which includes a tongue, and wherein the insert includes a pair of side edges, each of which has a groove configured to receive the tongue, thereby permitting axial movement of the insert relative to the tubular body.

11. The anoscope of claim 1, wherein the at least one elongated opening in the tubular body includes a pair of side edges and an end wall, and wherein the insert includes a distal edge configured to abut the end wall of the at least one elongated opening in the tubular body.

12. An anoscope for inspection and/or surgery, the anoscope comprising:
    a tubular body having a distal end and a generally flared proximal end and a cavity disposed therein, the tubular body including a suturing slot,
        wherein the suturing slot extends through the tubular body to the cavity,
        wherein the suturing slot begins at the proximal end of the tubular body and extends towards and terminates before the distal end of the tubular body, and
        wherein the suturing slot has an end wall and a pair of side edges defining a first width;
    an insert removably attached to the suturing slot in the tubular body, the insert including a pair of side edges and a distal edge configured to abut the end wall of the suturing slot, and the insert further including an excision slot having a second width that is less than the first width, the excision slot beginning at a proximal end of the insert and extending towards and terminating before a distal end of the insert such that the insert has a U-shape when viewed from the top; and
    a handle extending from the proximal end of the tubular body.

13. The anoscope of claim 12, wherein the suturing slot in the tubular body is generally rectangular when viewed from the top.

14. The anoscope of claim 12, wherein each of the side edges of the insert has a tongue for receipt within a respective groove in the side edges of the suturing slot in the tubular body, to permit axial movement of the insert relative to the tubular body.

15. The anoscope of claim 12, wherein each of the side edges of the suturing slot in the tubular body has a tongue for receipt within a respective groove in the side edges of the insert, to permit axial movement of the insert relative to the tubular body.

16. A kit for performing an excisional hemorrhoidectomy on a patient, the kit comprising:
    an anoscope that includes:
        a tubular body having an elongated opening extending from an outer surface to an inner surface of the tubular body, where the elongated opening begins at a proximal end of the tubular body and extends towards and terminates before a distal end of the tubular body and an insert removably attached to the elongated opening in the tubular body via a tongue and groove arrangement, the insert including an elongated opening beginning at a proximal end of the insert and extending towards and terminating before a distal end of the insert, such that the insert has a U-shape when viewed from the top, the elongated opening in the insert having a smaller width than the elongated opening in the tubular body;

a grasping instrument; and an excising device.

17. The kit of claim 16, wherein the proximal end of the tubular body of the anoscope includes a flared portion.

18. The kit of claim 16, wherein the elongated opening in the tubular body of the anoscope includes a pair of side edges, each side edge including a tongue, and wherein the insert of the anoscope includes a pair of side edges, each side edge having a groove configured to receive the tongue, thereby permitting axial movement of the insert relative to the tubular body.

19. The kit of claim 16, wherein the distal end of the tubular body of the anoscope is generally closed.

20. The kit of claim 16, wherein the elongated opening in the tubular body of the anoscope is generally rectangular when viewed from the top.

* * * * *